United States Patent [19]

Schaeffer

[11] 4,360,522

[45] Nov. 23, 1982

[54] PURINE DERIVATIVES

[75] Inventor: Howard J. Schaeffer, Raleigh, N.C.

[73] Assignee: Burroughs Wellcome Co., Research Triangle Park, N.C.

[21] Appl. No.: 874,067

[22] Filed: Feb. 1, 1978

Related U.S. Application Data

[60] Division of Ser. No. 718,105, Aug. 27, 1976, abandoned, which is a continuation-in-part of Ser. No. 662,900, Mar. 1, 1976, Pat. No. 4,199,574, and a continuation-in-part of Ser. No. 608,263, Aug. 27, 1975, abandoned.

[30] Foreign Application Priority Data

Sep. 2, 1974 [GB] United Kingdom .............. 38278/74

[51] Int. Cl.$^3$ .............................................. A61K 31/52
[52] U.S. Cl. .................................... 424/253; 424/200; 544/244; 544/265; 544/276; 544/277

[58] Field of Search .............. 544/277, 265, 276, 244; 424/200, 253

[56] References Cited

U.S. PATENT DOCUMENTS 4,146,715 3/1979 Schaeffer ............................ 544/277
4,199,574 4/1980 Schaeffer ............................ 544/244

Primary Examiner—Paul M. Coughlan, Jr.
Attorney, Agent, or Firm—Donald Brown

[57] ABSTRACT

9-Hydroxyethoxymethyl (and related) derivatives of certain 6-, and 2,6-substituted purines have been discovered to have potent anti-viral activities. Novel compounds and their pharmaceutically acceptable salts, pharmaceutical formulations containing the compounds of this invention, and the treatment of viral infections with these formulations are all disclosed. 9-(2-hydroxyethoxymethyl) guanine and 2-amino-9-(2-hydroxyethoxymethyl)adenine are examples of especially active compounds of this invention.

16 Claims, No Drawings

PURINE DERIVATIVES

This is a division of application Ser. No. 718,105, filed Aug. 27, 1976, now abandoned, which is a continuation in part of U.S. applications Ser. No. 662,900, filed Mar. 1, 1976, now U.S. Pat. No. 4,199,574, and Ser. No. 608,263, filed Aug. 27, 1975, now abandoned.

This invention relates to substituted purine compounds and their pharmaceutically acceptable salts and to methods of preparing them. In particular this invention relates to the 9-(2-hydroxyethoxymethyl) derivatives of purines such as adenine, guanine, thioguanine and 2,6-diaminopurine and the pharmaceutically acceptable salts of these compounds. In 1971, Schaeffer, et al. (J. Med. Chem., 14, 367 (1971)) reported the syntheses of several purine acyclic nucleosides in a study of adenosine deaminase enzymesubstrate interaction. 9-(2-Hydroxyethoxymethyl)adenine in particular was reported and its substrate activity with adenosine deaminase measured.

It has now been discovered that substituted purines of formula (1)

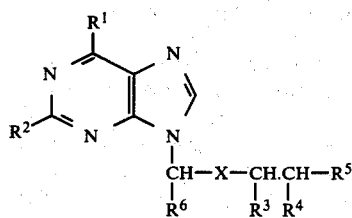

wherein X is oxygen or sulphur and $R^1$, $R^2$, $R^3$, $R^4$, $R^5$ and $R^6$ are various substituents as described herein, have antiviral activity against various classes of DNA and RNA viruses both in vitro and in vivo experiments. In particular the compounds are active as anti-virals against cytomegalovirus, adenovirus, in particular adenovirus 5, rhino virus, Mango virus and Sindbis virus. They are especially active as an anti-viral against vaccinia, and herpes viruses, including simplex, zoster and varicella, in mammals, which cause such diseases as for example herpetic keratitis in rabbits and herpetic encephalitis in mice.

According to the present invention there is provided a compound of formula (I) wherein X is sulphur or oxygen, $R^1$ is hydrogen, halogen, hydroxy, alkoxy, azide, thio, alkylthio, amino, alkylamino or dialkylamino; $R^2$ is hydrogen, halogen, alkylthio, acylamino, amino or azide; $R^3$ is hydrogen, straight or branch chain or cyclic alkyl, hydroxyalkyl, benzyloxyalkyl or phenyl; $R^4$ is hydrogen, hydroxy or alkyl; $R^5$ is hydrogen, hydroxy, amino, alkyl, hydroxyalkyl, benzyloxy, benzoyloxy, benzoyloxymethyl, sulphamoyloxy, phosphate, straight or branched chain or cyclic acyloxy having from 1 to 8 carbon atoms, or substituted carbamoyl group of formula NH.CO—Z wherein Z is alkyl, aryl or aralkyl optionally substituted by one or more of sulphonyl, amino, carbamoyl or halogen; $R^6$ is hydrogen or alkyl, provided that when X is oxygen and $R^2$, $R^3$, $R^4$ and $R^6$ are hydrogen, $R^1$ is not amino or methylamino when $R^5$ is hydrogen or hydroxy, or a salt thereof especially in the form of a pharmaceutically acceptable salt.

Compounds of formula (I), wherein X is sulphur or oxygen; $R^1$ is hydrogen, halogen, hydroxy, alkoxy, azide, thio, alkylthio, amino, alkylamino or dialkylamino; $R^2$ is hydrogen, halogen, amino or azide; $R^3$ is hydrogen, straight or branched chain or cyclic alkyl, hydroxyalkyl, benzyloxyalkyl or phenyl; $R^4$ is hydrogen, hydroxy or alkyl; $R^5$ is hydrogen, hydroxy, amino, alkyl, hydroxyalkyl, benzoyloxy, benzoyloxymethyl, benzyloxy, sulphamoyloxy, phosphate, carboxypropionyloxy, acetoxy, or substituted carbamoyl group of formula NH.CO—Z wherein Z is alkyl, aryl or aralkyl optionally substituted by one or more of sulphonyl, amino, carbamoyl, halogen; $R^6$ is hydrogen, or alkyl, provided that when X is oxygen and $R^2$, $R^3$, $R^4$ and $R^6$ are hydrogen, $R^1$ is not amino or methylamino when $R^5$ is hydrogen or hydroxy, or a salt thereof, especially in the form of a pharmaceutically acceptable salt are preferred.

Cyclic acyloxy is defined to include alicyclic acyloxy and aromatic acyloxy, i.e. aroyloxy such as benzoyloxy.

Especially preferred are compounds of formula (I) as defined above wherein $R^5$ is straight or branched chain acyloxy containing 1 to 5 carbon atoms, e.g. formyloxy, acetyloxy, propionyloxy, and pivaloyloxy, or an aroyloxy, e.g. benzoyloxy, and most especially wherein $R^1$ is amino or hydroxy, $R^2$ is amino, and $R^3$, $R^4$, and $R^6$ are hydrogen, and their salts, especially their pharmaceutically acceptable salts.

Also especially preferred are compounds of formula (I) as defined above wherein $R^5$ is carboxyacyloxy containing 4 to 6 carbon atoms, e.g. carboxypropionyloxy (i.e. 3-carboxypropionyloxy), carboxybutyryloxy (i.e. 4-carboxybutyryloxy) and carboxyvaleryloxy (i.e. 5-carboxyvaleryloxy), and most especially wherein $R^1$ is amino or hydroxy, $R^2$ is amino, and $R^3$, $R^4$, and $R^6$ are hydrogen and most preferred wherein $R^1$ is hydroxy, $R^2$ is amino, and $R^3$, $R^4$, and $R^6$ are hydrogen, and their salts, especially their pharmaceutically acceptable salts.

Compounds of formula (I) as defined above wherein X is oxygen; $R^1$ is hydrogen, halogen, hydroxy, alkoxy, thio, alkylthio, amino, alkylamino, dialkylamino or azide; $R^2$ is hydrogen, halogen, amino or azide; $R^3$ is hydrogen, straight or branched chain or cyclic alkyl, hydroxyalkyl or phenyl; $R^4$ is hydrogen, or hydroxy; $R^5$ is hydrogen, hydroxy, benzoyloxy, hydroxyalkyl, amino, carboxypropionyloxy, acetoxy, benzyloxy, benzoyloxymethyl, phosphate, sulphamoyloxy, substituted carbamoyl group of formula NH.CO—Z where Z is alkyl, aryl or aralkyl optionally substituted by one or more of sulphonyl, amino, carbamoyl, halogen; $R^6$ is hydrogen, or alkyl, provided that $R^5$ is hydroxy only when $R^1$ is amino, hydroxy, alkylamino, alkylthio, or dialkylamino, and $R^2$ is amino and $R^6$ is hydrogen; $R^5$ is alkyl-hydroxy only when $R^1$ is hydroxy; $R^5$ is hydrogen only when $R^1$ is hydroxy or halo; when $R^5$ is benzoyloxy $R^2$ is not halogen; $R^5$ is acetoxy only when $R^1$ is hydroxy or amino and $R^2$ is amino or both $R^1$ and $R^2$ are halogen; $R^5$ is a substituted carbamoyl of formula NH.CO—Z wherein Z is a group $CH(NH_2)C_2C_6H_5$ only when $R^1$ is dialkylamino; except that when $R^5$ is hydroxy and $R^1$ is alkylamino then $R^2$ is not hydrogen; or a salt thereof, especially in the form of a pharmaceutically acceptable salt are particularly preferred.

In particular compounds of formula (1), as hereinbefore defined, where X is oxygen, $R^1$ is halogen, amino, hydroxy or alkylthio; $R^2$ is amino, $R^5$ is hydroxy, benzoyloxy, carboxypropionyloxy, acetoxy or hydroxyalkyl and $R^3$, $R^4$ and $R^6$ are hydrogen, provided that $R^5$ is hydroxyalkyl only when $R^1$ is hydroxy and $R^5$ is acetoxy only when $R^1$ is hydroxy or amino, are most preferred and have been found to be highly active. Compounds where X is sulphur, $R^1$ is halogen, amino or alkylamino and $R^2$, $R^3$, $R^4$, $R^5$ and $R^6$ are hydrogen have also been found to be highly active.

Additionally, the compound where X is oxygen, $R^1$ is hydroxy, $R^2$ is amino, $R^3$, $R^4$ and $R^6$ are hydrogen and $R^5$ is a formyloxy group has been found to be highly active.

The preferred halogen substituent is chlorine. As used herein and throughout the specification the term alkyl is denoted to mean 1 to 12 carbon atoms, preferably 1 to 8 carbon atoms.

Salts which are especially convenient for therapeutic use are salts of pharmaceutically acceptable organic acids such as lactic, acetic, malic, or p-toluenesulfonic acid as well as salts of pharmaceutically acceptable mineral acids such as hydrochloric or sulfuric acid.

In a second aspect of the present invention there is provided a method of preparing a substituted purine of formula (I) or an acid addition salt thereof

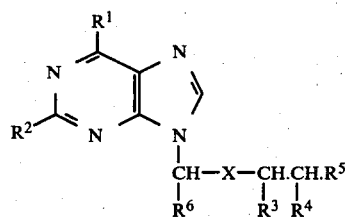

(I)

wherein X, $R^1$, $R^2$, $R^3$, $R^4$, $R^5$ and $R^6$ are hereinbefore defined provided that when X is oxygen and $R^2$, $R^3$, $R^4$ and $R^6$ are hydrogen, $R^1$ is not amino or methylamino when $R^5$ is hydrogen or hydroxy; or a salt thereof, especially a pharmaceutically acceptable salt thereof characterised in that:

(a) where in the compound of formula (I) $R^5$ is amino or hydroxy, a protective group Y is replaced in a compound of formula (II) by an amino or hydroxy group;

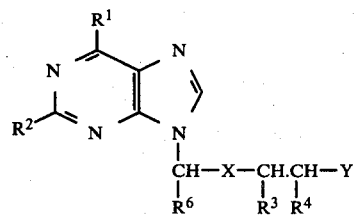

(II)

(b) a compound of formula (III) wherein M and G are precursors of groups $R^1$ and $R^2$ respectively is converted

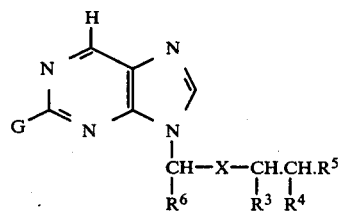

(III)

into a compound of formula (I) where $R^1$ and $R^2$, have the values as defined above;

(c) a compound of formula (IV)

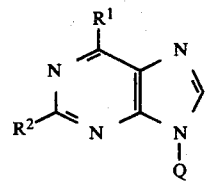

(IV)

is reacted with a compound of formula (V)

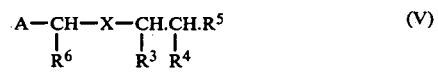

(V)

wherein A is a leaving group and Q is an hydrogen atom or a leaving group;

(d) a ring is closed in a precursor compound having either the pyrimidine or imidazole ring incompletely formed;

(e) a blocking group is removed from a compound of formulation (I) wherein one or both of $R^1$ and $R^2$ is blocked; and where the product of said reaction is a base, optionally converting a compound of formula (I) into an acid addition salt thereof, or where the product is a salt of a compound of formula (I), optionally converting said salt into its base or another salt thereof.

In the case of method (a) the 9-ether chain is blocked terminally by a protective group Y which may be an ester, eg an acyloxy group, an amide, eg a phthalimide group, or an arylmethoxy group, eg benzyloxy. In the first instance the acyl group may be aliphatic eg acetyl, or aromatic eg benzoyl, both types of acyl group being removed by mild basic hydrolysis. In general warming with aqueous methylamine will suffice to bring about the deblocking.

Arylmethoxy blocking groups, such as benzyloxy, are removed by hydrogenolysis, either catalytically, as by hydrogen and Raney nickel or palladium-on-charcoal, or chemically, as by sodium in liquid ammonia. When sodium in liquid ammonia is used, an excess of ammonia serves as solvent. For catalytic hydrogenolysis an alkanol is the preferred solvent, although a number of inert, eg non halogen and non-sulphide or mercapto containing solvents may be used provided they dissolve the acyl-blocked substrate, eg such solvents as benzene, tetra hydrofuran or dioxane.

Conversion of a compound of formula (III)

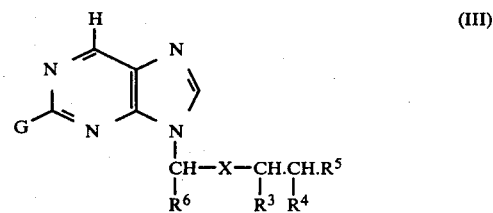

(III)

into a compound of formula (I), by method (b), can be achieved in numerous different ways. For example one or both of G and M can be converted into a halogen atom by halogenation; into an hydroxy groups by hydrolysis; into a thio or alkylthio group by sulphuration; into an hydrogen atom by reduction or desulphuration; or by formation of the azide. All such methods are well known and can be found in "Heterocyclic compounds—Fused Pyrimidines Part II Purines Ed. by D. J. Brown (1971) published Wiley-Interscience".

Alternatively conversion can be brought about by using enzymes, for example adenosine deaminase efficiently converts a 2,6 diamino compound to guanine $R^1=OH$ $R^2=NH_2$, in an aqueous suspension at about 37° C. and initial pH of about 7.0.

Those compounds that contain precursors of groups $R^1$ and $R^2$ and can be converted into compounds of formula (I) can be considered as intermediates in the synthesis of those compounds.

The intermediate of formula (IX)

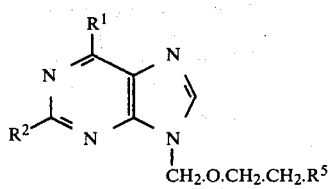

wherein $R^1$ is a hydroxy or amino group, $R^2$ is a hydrogen or halogen atom, or hydrazino group, and $R^5$ is a hydroxy or phthalimido group; and of formula (X)

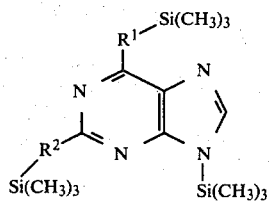

wherein $R^1$ is an NH group and $R^2$ is an NH group, are novel compounds and are therefore provided in a further aspect of the invention.

In method (c) the leaving group A is a reactive residue of an organic or inorganic acid, and may therefore be a halogen atom, or a carboxylate group, and Q is a hydrogen atom or an acyl group. The preferred method comprising the condensation of a purine having the desired 2- and 6-substitution with an acyl or aralkyl-blocked 2-haloalkoxyethanol for instance 2-benzoyloxyethoxymethyl chloride, in a strong polar solvent such as DMF (dimethylsulphoxide) or hexamethylphosphoramide, and in the presence of a base such as triethylamine or potassium carbonate. The reaction is preferably carried out at room temperature over an extended period of time ie several days may be required to give reasonable yields.

Alternatively a thermal condensation, eg fusion reaction, may be carried out to give the product directly. For this reaction a suitably substituted parine is heated together with an acyloxy-alkoxymethyl carboxylate eg 2-oxa-1-4-butanediol diacetate, in the presence of a catalytic amount strong acid such as sulphuric acid. Temperatures in excess of 100° C. are generally required, but they should preferably not be greater than about 200° C. in order to minimise decomposition. The temperature should be selected such that the mixture of reactants fuse before they undergo decomposition.

The fusion reaction may also be carried out under substantially the same condition as above, with perhaps somewhat lower temperatures, between a 9-acylpurine and the alkoxmethyl carboxylate or halide. Alternatively the fusion reaction can be carried out using the diester, for instance 2-acetoxyethoxymethyl acetate.

Method (d) involves the ring closure of either the imidazole or pyrimidine ring to give the final product. In the case of the imidazole ring this may be achieved by reaction of the suitably substituted precursor with a one carbon reagent, such as triethylorthoformate, under for example mildly acidic conditions, at a temperature of about 25° C. and for several hours. A suitable precursor is a substituted pyrimidine of formula (VI)

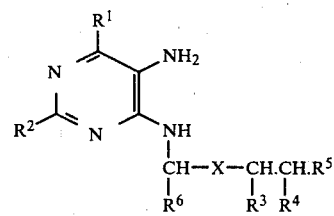

An alternative reagent to use is diethoxymethyl acetate, when neutral conditions at about 100° C. for about 10-15 minutes are preferred.

The ring closure of the pyrimidine ring is similar to that for the imidazole ring except that the carbon reagent being added is generally substituted, for example by amino. The blocked, substituted carbon is first attached to the 2-amino group on a precursor of formula (VII)

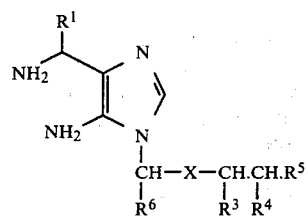

and then deblocked and cyclized. Cyclization may be achieved in some cases by treatment with acid, however this should be done as close to neutral as possible. In other cases a compound of formula (VII) can be closed by reaction with one of the standard one carbon reagents, under mild conditions. (See. J. Org. Chem. 81 (1959) p. 6021 A. Yamazaki et al). It is important in this method that the substitution at the 2 position, is $R^2$ of formula I, is introduced during ring closure. Suitable substituents in the 6 position, ie $R^1$, are limited, to such groups as thio, amino or hydroxy.

In method (e) substituents $R^1$ and $R^2$ may be blocked by for instance trimethylsilyl groups. Such a compound will be the product of the condensation of a trimethylsilylated purine and an ester or diester as in method (c). Such blocking groups are very labile and can be removed by solvolysis with alcoholic or aqueous ammonia, or by alcoholysis.

Alternatively the mercuric chloride salt of a purine can be prepared in the presence of alkali and then condensed with a haloether in solvent of the aromatic organic type. Prior to preparation of the salt however all reactive substituents on the purine must be blocked, and therefore the last step in this method is the unblocking of the blocked substituents.

In another method, which combines methods (a) and (b) solvolytic deblocking may be effected at the same time as replacement of a purine ring leaving group e.g. halogen, such as by the reaction with liquid ammonia. In this case the leaving group or the purine nucleus is replaced by an amino group at the same as deblocking the side chain, see method (a).

In another aspect of the invention there is provided a pharmaceutical composition or preparation comprising a compound of formula (I), wherein X, R, $R^2$, $R^3$, $R^4$, $R^5$ and $R^6$ are hereinbefore defined, when $R^6$ is alkyl group it has from 1 to 8 carbon atoms and in all other cases when the substituents have an alkyl moiety it has from 1 to 4 carbon atoms; or a pharmaceutically acceptable salt thereof; together with a pharmaceutically acceptable carrier therefor. In particular aspect the pharmaceutical composition comprises a compound of formula (I) in effective unit dosage form.

As used herein the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops etc., depending on whether the preparation is used to treat internal or external viral infections.

For internal infections the compositions are administered orally or parenterally at dose levels, calculated as the free base, of about 0.1 to 250 mg per kg, preferably 1.0 to 50 mg per kg, of mammal body weight, and are used in man in a unit dosage form, administered, eg a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavouring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10% more preferably 0.1 to 7%, most preferably 0.2% w/v. The solution may contain antioxidants, buffers, etc.

Alternatively for infections of the eye, or other external tissues e.g. mouth and skin the compositions are preferably applied to the infected part of the body of the patient as a topical ointment or cream. The compounds may be presented in an ointment, for instance with a water soluble ointment base, or in a cream, for instance with an oil in water cream base, in a concentration of from about 0.1 to 10%, preferably 0.1 to 7%, most preferably 1% w/v.

Of the compounds of formula (I), 9-(2 hydroxyethoxymethyl)guanine ($R^1$=OH, $R^2$=NH$_2$), 2-amino-9-(2-hydroxyethoxymethyl)adenine ($R^1$=$R^2$=NH$_2$) and their esters are most preferred, particularly because of their extremely high antiviral activity against herpes viruses. Additionally 2 amino-6-chloro-9((2-benzoyloxyethoxy)methyl)purine, 9(2-benzoyloxyethoxymethyl) guanine, 9-(3-hydroxypropoxymethyl)guanine, 2 amino-6-methylthio-9-(2-hydroxyethoxymethyl)purine, 9-{2-(3-carboxypropionyloxy)ethoxymethyl}guanine, 9-(2-acetoxyethoxymethyl)-2,6-diamino purine, 6-chloro-9-ethylthiomethyl purine, 9-ethylthiomethyladenine, 9-ethylthiomethyl-6-methylamino-purine also show high activity against herpes viruses and vaccinia.

In yet a further aspect of the invention there is provided a method of treating viral infections in mammals which comprises the administration of an effective non-toxic anti-viral amount, as hereinbefore defined of a substituted purine of formula (I), or a pharmaceutically acceptable salt thereof. Administration is preferably by topical application or by the oral or parenteral route.

The invention will now be illustrated with reference to the following examples.

EXAMPLE 1

6-Chloro-9-(2-benzoyloxyethoxymethyl)purine

A solution of benzonitrile (103 g) in ethylene glycol (310 g) was heated at reflux under substantially anhydrous conditions for 3 days. The reaction mixture was cooled and added to a mixture of ice and water (about 300 ml). The resulting mixture was extracted with ether (3×300 ml) and the combined ether extract backwashed with water (2×300 ml) and then with a saturated sodium chloride solution (300 ml). The ether solution was dried over anhydrous sodium sulfate. The ether was evaporated and the residual oil distilled to give 108 g (65% of theoretical) of ethylene glycol monobenzoate, b.p. 132°–135° C./1.5 mm Hg.

A cold (0° C.) mixture of ethylene glycol monobenzoate (166 g) and paraformaldehyde (30 g) in dry dichloroethane was saturated with dry HCl with stirring for 3 hours. The pinkish red liquid was dried over calcium chloride and the volatile components removed on a rotary evaporator at 30° C. to give 1-benzoyloxy-2-chloromethoxyethane (215 g). The Infra-Red spectrum indicated the absence of a hydroxyl group.

Following substantially the procedure of Schaeffer, et al. supra but with minor modifications, 1-benzoyloxy-2-chloromethoxyethane (4.4 g) was added with stirring to a dry solution of 6-chloropurine (3.1 g) and triethylamine (6.5 ml) in dimethylformamide (50 ml). The reaction was exothermic, immediately precipitating triethylamine hydrochloride. The reaction mixture was stirred at room temperature for 24 hours and filtered. The filtrate was evaporated on a rotary evaporator at 70° C. The remaining thick amber oil was dissolved in the minimum amount of benzene and purified by column chromatography using a silica gel column. Benzene elution removed a trace of an unidentified material. Elution with ether first removed a small amount of ethylene glycol monobenzoate and then 6-chloro-9-(2-benzoyloxyethoxymethyl)purine. Recrystallization from ether gave a white material, m.p. 108.5°–111° C.

EXAMPLE 2

9-(2-Hydroxyethoxymethyl)adenine (I; $R^1$=NH$_2$, $R^2$=H)

A solution of 6-chloro-9-(2-benzoyloxyethoxymethyl)purine (50 g) and ammonia (31 g) in methanol (120 ml) was heated in a bomb at 95° C. for 18 hours. The reaction mixture was removed from the bomb and the solvent evaporated under reduced pressure at 50° C. The resulting solid was triturated first with water and then, after drying, with chloroform. The solid, 9-(2-hydroxyethoxymethyl)adenine, was retained, and the aqueous triturate was extracted several times with chloroform. The aqueous extracts were treated with a strongly basic ion exchange resin and then evaporated to dryness under reduced pressure. The remaining solid was combined with that from the trituration step and recrystallized from isopropanol to give 22 g (70% of theoretical) of white 9-(2-hydroxyethoxymethyl)adenine, m.p. 199.5°-200° C.

EXAMPLE 3

2-Chloro-9-(2-hydroxyethoxymethyl)adenine

Following the procedure of Example 1,2,6-dichloropurine was condensed with 1-benzoyloxy-2-chloromethoxyethane to give a 41% yield of 2,6-dichloro-9-(2-benzoyloxy ethoxymethyl)purine, m.p. 121°-125° C. This was treated according to the procedure of Example 2 to give simultaneous ammonolysis of the 6-chloro and benzoyloxy groups yielding 2-chloro-9-(hydroxyethoxymethyl)adenine, in 94% yield, m.p. 188°-190° C. after recrystallization from isopropanol.

EXAMPLE 4

2-Amino-9-(2-hydroxyethoxymethyl)adenine I; $R^1=R^2=NH_2$

2-Chloro-9-(2-hydroxyethoxymethyl)adenine (0.83 g) was added with stirring to 95% hydrazine (11 ml) and the resulting solution stirred 1 hour under nitrogen. Excess hydrazine was removed by distillation in a rotary evaporator at a bath temperature of 30° C. followed by co-evaporation twice with ethyl acetate. The residue was thoroughly triturated with methanol to give a quantitative yield (0.8 g) of white to cream colored-2-hydrazino-9-(2-hydroxyethoxymethyl)adenine, m.p. 220°-222° C.

A solution of this hydrazine derivative (0.85 g) in 5% aqueous acetic acid (30 ml) was chilled to 5°-8° C., and a cold (0° C.) solution of sodium nitrite (0.3g) in water (5 ml) was added in one portion. The reaction mixture was stirred in an ice bath for one hour and then filtered, washed with cold water and dried at room temperature to give 2-azido-9-(2-hydroxyethoxymethyl)adenine (0.86 g). Recrystallization from water gave a light mauve product, m.p. 191°-192° C.

A mixture of 2-azido-9-(2-hydroxyethoxymethyl)adenine (0.41 g) and 10% palladium on charcoal (80 mg) in ethanol (41 ml) was shaken under hydrogen at 50 psi for 3.5 hours. The catalyst as removed by filtration through a celite pad and washed thoroughly with ethanol and water. The solvent was removed by evaporation under reduced pressure giving a quantitative yield (0.37 g) of nearly pure (one spot on TLC) 2-amino-9-(2-hydroxyethoxymethyl)adenine, m.p. 183°-184° C. after recrystallization from n-propanol.

EXAMPLE 5

9-(2-Hydroxyethoxymethyl)quanine (I; $R^1=OH$, $R^2=NH_2$)

Solid sodium nitrite (0.97 g) was added at room temperature with stirring over a period of one hour to a solution of 2-chloro-9-(2-hydroxyethoxymethyl)adenine (0.5 g) in glacial acetic acid (10 ml). The reaction mixture was stirred for an additional 4½ hours. The white solid was removed by filtration, washed with cold acetic acid and then well triturated with cold water to remove the sodium acetate present. The solid product was retained. The combined acetic acid filtrate and wash was evaporated at reduced pressure and 40° C. bath temperature and the residual oil triturated with cold water. The resulting solid material was combined with the previously isolated solid and the combined solids dried and recrystallized from ethanol to give 2-chloro-9-(2-hydroxyethoxymethyl)hypoxanthine (0.25 g), m.p. >310° C. Elemental analysis and NMR spectrum were consistent with this structure.

A mixture of 2-chloro-9-(2-hydroxyethoxymethyl)-hypoxanthine (0.375 g) and methanol (80 ml) saturated with anhydrous ammonia was heated in a bomb at 125° C. for 5 hours. The bomb was cooled in an ice bath and the reaction mixture removed. Solvent and excess ammonia were removed under reduced pressure at 50° C. After the residue was triturated with cold water to remove the ammonium chloride formed, the remaining solid was dried and then recrystallized from methanol to give pure 9-(2-hydroxyethoxymethyl)guanine (0.24 g), m.p. 256.5°-257° C.

EXAMPLE 6

9-(2-Hydroxyethoxymethyl)guanine (I; $R^1=OH$, $R^2=NH_2$)

A mixture of guanine (2.0 g), ammonium sulfate (1.5 g), and hexamethyldisilazane (126 g) was heated at reflux under nitrogen overnight. Excess hexamethyldisilazane was removed by distillation at reduced pressure. Dry benzene (10 ml) was added to the residual oil and any remaining ammonium sulfate removed by filtration. To this solution was added triethylamine (4 ml) and a solution of 2-benzoyloxyethoxymethyl chloride (2.8 g) in dry benzene (15 ml) and the mixture heated at reflux under nitrogen overnight. The solvent was evaporated in a rotary evaporator at reduced pressure and the residue dissolved in 95% ethanol. The solution was warmed on a steam bath for ½ hour to effect hydrolysis of the silyl groups. The ethanol was then evaporated and the residual solid thoroughly washed with water, filtered and dried. Recrystallization from methanol and then from water (residual guanine was insoluble in the hot solvents and was removed by filtration) afforded 9-(2-benzoyloxyethoxymethyl)guanine (0.58 g., 14% of theroetical), m.p. 222°-226° C. A later condensation of the tris-(trimethylsilyl)guanine with a 60% excess of 2-benzoyloxyethoxymethyl chloride gave a 32% yield of 9-(2-benzoyloxyethoxymethyl)guanine.

9-(Benzoyloxyethoxymethyl)guanine (0.58 g) and methanol (80 ml) saturated with ammonia were heated in a bomb at 80° C. for 16 hours. The reaction mixture was removed from the bomb and the solvent evaporated under reduced pressure. The residue was thoroughly washed with ether and then recrystallized from methanol to give 9-(2-hydroxyethoxymethyl)guanine (0.31 g., 75% of theoretical), m.p. 256.5°-257° C.

EXAMPLE 7

2-Amino-9-(2-hydroxyethoxymethyl)adenine (I; $R^1=R^2=NH_2$)

A mixture of 2-chloro-9-(2-hydroxyethoxymethyl)adenine (4.4 g) and liquid ammonia (40 ml) was heated at 120° C. in a bomb for 19 hours. The reaction mixture was removed from the bomb and excess ammonia removed in vacuo. The residue was partitioned between ether and water and the aqueous layer washed twice more with ether and once with chloroform. The aqueous solution was then treated with an excess of a strongly basic ion exchange resin to convert the ammonium chloride to ammonia and evaporated to dryness in vacuo. The residue was dissolved in a minimal amount of ethanol, Florisil (Registered Trade Mark) (10g) added, and the mixture evaporated in dryess. The residue was transferred to a prepared column of Florisil in chloroform and eluted with 5% methanol/95% chloroform (v/v). Fractions (30 ml) were collected and examined by TLC (silica gel plates developed in 10% methanol/90% chloroform) for the presence of product. The first 40 fractions contained starting material but no product and were discarded. Succeeding fractions which were found to contain the desired product were combined and evaporated to dryness. The residue was recrystallized from ethanol (with activated charcoal treatment) and from n-propanol to give 2-amino-9-(2-hydroxyethoxymethyl)adenine (0.5 g, 12% of theoretical), m.p. 183°–184° C.

Florisil is an activated magnesium silicate widely used in column chromatography.

EXAMPLE 8

2-Amino-6-chloro-9-(2-benzoyloxyethoxymethyl)purine

A suspension of potassium carbonate (4.1 g) and 2-amino-6-chloropurine (5.0 g) in dry dimethylformamide (120 ml) was stirred for 20 minutes. 2-Benzoyloxyethoxymethyl-chloride (6.3 g) was added and the resulting pink suspension stirred at room temperature for 6 days. The reaction mixture was then poured into a mixture of ice and water (210 ml) with vigorous stirring. The aqueous mixture, was extracted with chloroform (3×200 ml), and the chloroform solution obtained was washed with a 5% acetic acid solution and then twice with water. The chloroform solution was dried over anhydrous sodium sulfate and evaporated in vacuo. The residue was redissolved in a minimal amount of chloroform and the resulting solution applied to a column containing silica gel (200 g) in chloroform. The column was eluted with 2% methanol/98% chloroform and the eluant collected in 30 ml cuts. The fractions containing 2-amino-6-chloro-9-(2-benzoyloxyethoxymethyl)purine (determined by TLC) were combined, evaporated and the residue recrystallized from benzene to give 2-amino-6-chloro-9-(2-benzoyloxyethoxymethyl)purine (2.0 g., m.p. 130°–133.5° C.).

EXAMPLE 9

9-(2-Hydroxyethoxymethyl)thioguanine (I; $R^1$=SH, $R^2$=NH$_2$)

Thiourea (0.28 g) was added to a refluxing solution of 2-amino-6-chloro-9-(2-benzoyloxyethoxymethyl)purine (1.27 g) in isopropanol (40 ml). The reaction mixture was heated at reflux for 1½ hours and then chilled. 9-(2-benzoyloxyethoxymethyl)thioguanine (0.58 g, m.p. 199°–202° C.) was removed by filtration. This was added to 40 ml of aqueous ammonia (about 7 N) and the mixture heated on a steam bath for 10 minutes and then stirred overnight at room temperature. The water and ammonia were removed in vacuo and the residue triturated with acetone and then with ether to remove benzamide. The remaining solid was recrystallized twice from water to give yellow flakes of 9-(2-hydroxyethoxymethyl)thioguanine (0.26 g, m.p. 251°–254° C.).

EXAMPLE 10

9-(2-Hydroxyethoxymethyl)guanine (I; $R^1$=OH, $R^2$=NH$_2$)

To a solution of 2-amino-9-(2-hydroxyethoxymethyl)adenine (0.22 g) in water (30 ml) was added a suspension of adenosine deaminase in aqueous ammonium sulfate (0.44 ml, containing 4.4 mg of the enzyme). The reaction mixture, which initially had a pH of 7.0, was heated at 37° C. for 18 hours, at which time the pH was 8.5 and TLC (silica gel plates developed in 15% methanol - 85% chloroform) indicated a single product different from starting material. The reaction mixture was thoroughly chilled in an ice bath and the resulting white solid removed by filtration and thoroughly washed with cold water. The product was dried at 100° C./0.1 mm Hg for 16 hours to give 0.20 g of 9-(2-hydroxyethoxymethyl)guanine. ¼ H$_2$O, the structure of which was confirmed by m.p., TLC, U.V., NMR and mass spectroscopy analysis. Recrystallization from methanol gave the anhydrous 9-(2-hydroxyethoxymethyl)guanine.

EXAMPLE 11

2-Amino-9-(2-hydroxyethoxymethyl)adenine hydrochloride

2-Amino-9-(2-hydroxyethoxymethyl)adenine (0.25 g) was dissolved in hot ethanol (50 ml) and the solution cooled in an ice bath. To the cool solution was added sufficient HCl-saturated ethanol to give a pH of 1.0 Dry ether (50 ml) was then added and the mixture thoroughly chilled. The resulting flesh-colored solid was removed by filtration and washed with cold ethanol. Recrystallization from methanol yielded 2-amino-9-(2-hydroxyethoxymethyl)adenine hydrochloride (0.21 g., 74% of theoretical), m.p. 207°–211° C. Elemental analysis and NMR support this structure.

EXAMPLE 12

Properties of 9-(2-hydroxyethoxymethyl)guanine 9-(2-hydroxyethoxymethyl)guanine was determined by U.V. to be soluble in either water or 0.1 N aqueous hydrochloric acid to the extent of about 0.2%. It was stable in either 0.01 N or 0.1 N aqueous hydrochloric acid at 26° C. and at 37° C., showing no indication of hydrolysis after one week. However, in 1 N aqueous hydrochloric acid at either 26° C. or 37° C., it slowly hydrolyzed to guanine within one week.

13. Preparation of 2-amino-9-(2-hydroxyethoxymethyl)adenine 2,6-dichloro-9-(2-benzoyloxyethoxymethyl)purine 10 g, sodium azide 3.5 g and 54 ml. of 1:1 (v/v) ethanol-water were refluxed with stirring for 3½ hours at 110°–120° C. TLC of reaction mixture shows complete reaction. On overnight cooling the oil solidified and was filtered, washed with ethanol and water and recrystallized from ethanol. Quantitative yield m.p. 124°–125° C. Compound is labile in aqueous base and sensitive to sunlight.

1.2 g of 2,6-diazido-9-(2-benzoyloxyethoxymethyl)purine was dissolved in 150 ml. 1:1 methanol tetrahydrofuran and the solvent was put in Paar hydrogenation apparatus containing 33 mg. of 10% palladium charcoal which had been wetted with water and shaken under 50 psi hydrogen for 4.5 hours. The catalyst was filtered and washed well with water and methanol TLC showed complete reduction. Solution was evaporated to dryness giving a yield of 87% of 2,6-diamino intermediate.

The residue was dissolved in 40% aqueous methylamine minimum amount and was heated for ½ hour on a steam bath, cooled and extracted 3 times with an equal volume of ether. The ether extracts were back-washed with water and the combined aqueous phase evaporated to dryness. The residue was recrystallized from ethanol to give 89% yield of the compound 2-amino-9-(2-hydroxyethoxymethyl)adenine m.p. 182°–183.5° C.

14. Preparation of 2,6-Dichloro-9-(2-acetyloxyethoxymethyl)purine 2,6-Dichloropurine 5.5 g and 2-oxa-1,4-butanediol diacetate 513 g were placed in a flask and partially evacuated and then heated to 138° C., initially the mixture was too thick to stir but gradually gave rise to a melt which was stirred, and after 20 minutes was completely melted and the reaction mixture heated for 10 minutes more (total heat time=30 minutes). The mixture was then cooled to room temperature and para-toluenesulphonic acid 150 mg was added, the vacuum reapplied and heating resumed with stirring. After 20 minutes heating vigorous bubbling was noted; the mixture was cooled to room temperature; chloroform was added, and the solution was extracted once with saturated aqueous sodium bicarbonate and once with water. The chloroform phase was dried over anhydrous sodium sulphate and evaporated. The residual oil was dissolved in benzene and applied to a column of 200 g. of silica gel in benzene. Benzene elution removed the acetate by-products. Ether elution gave 2,6-dichloro-9-(2-acetyloxyethoxymethyl)purine (64% yield). Recrystallization from benzene gave lustrous white flakes, m.p. 96°–99° C.

EXAMPLE 15

2,6-Diamino-9-(2-benzoyloxyethoxymethyl)purine

A mixture of 2,6-diaminopurine monohydrate (2.0 g), ammonium sulfate (1.32 g), and hexamethyldisilizane (100 g) was heated at reflux under nitrogen for 18 hours. The solvent was evaporated under reduced pressure and the residual oil dissolved in a minimal amount of benzene. To the benzene solution was added 2-benzoyloxyethoxymethyl chloride (2.56 g), triethylamine (2 ml) and benzene (55 ml). This reaction mixture was heated at reflux under nitrogen for 18 hours. Additional 2-benzoyloxyethoxymethyl chloride (2.56 g) and triethylamine (2 ml) were added, and heating at reflux was continued for an additional 6 hours. The solvent was evaporated under reduced pressure and the residue digested on a steam bath for 30 minutes in 95% ethanol (40 ml). The solvent was evaporated and the gummy residue recrystallized from ethanol, twice from methanol and finally from water to give 2,6-diamino-9-(2-benzoyloxyethoxymethyl)purine as a yellow solid, m.p. 205° C., in 7.5% yield.

EXAMPLE 16

2-Amino-6-benzyloxy-9-(2-hydroxyethoxymethyl)purine

A solution of sodium benzylate in benzyl alcohol was prepared from sodium (2.58 g) and benzyl alcohol (28 ml). The solution was heated to 120° C. and 2-amino-6-chloro-9-(2-benzoyloxyethoxymethyl)purine (3.47 g) was added over a 10 minute period. The reaction mixture was heated overnight with stirring at 120°–130° C., and then poured into a mixture of ice and water. The resulting mixture was extracted thoroughly with chloroform. The aqueous phase was neutralized with acetic acid, giving a white precipitate which was recrystallized from methanol and then from water to give analytically pure 2-amino-6-benzyloxy-9-(2-hydroxyethoxymethyl) purine, m.p. 291°–292° C. (dec.) in 50% yield.

This compound may be reductively cleaved, e.g. with hydrogen, palladium/charcoal in methanol, to give 9-(2-hydroxyethoxymethyl)guanine.

EXAMPLE 17

9-(2-Hydroxyethoxymethyl)guanine.

2-Mercaptoethanol (0.75 ml) dissolved in 1 M methanolic sodium methylate (7.5 ml) was added to 2-amino-6-chloro-9-(2-benzoyloxyethoxymethyl)purine (0.89 g) in methanol (150 ml). The reaction mixture was heated at reflux for 3 hours under nitrogen. The solvent was evaporated under reduced pressure and the residue dissolved in water. The aqueous solution was heated on a steam bath for 2 hours, chilled, and acidified to pH 5.0 with acetic acid. The resulting white solid was removed by filtration, washed well with ice cold water and ether, and then recrystallized from methanol to give a 45% yield of 9-(2-hydroxymethoxymethyl)guanine.

EXAMPLE 18

9-Ethylthiomethyladenino

A reaction mixture containing chloromethyl ethyl sulfide (5.53 g), 6-chloropurine (7.73 g) and triethylamine (5.57) in dimethylformamide (50 ml) was allowed to stand at room temperature for three days. It was filtered and the filtrate evaporated. The semi-solid residue was dissolved in chloroform (ca. 80 ml), placed on a column of Florisil(activated magnesium silicate) (360 g) in chloroform, and eluted with chloroform. The initial eluate (ca. 500 ml) was discarded; the next 2.8 liters were collected and evaporated. Ligroin (ca. 50 ml) was added to the residual oil, the mixture chilled, and the resulting off white crystals of 6-chloro-9-ethylthiomethylpurine collected by filtration and washed with ligroin; yield 3.3 g (m.p. 78°–81° C.). Recrystallization from etherligroin gave white needles, m.p. 81°–82.5° C.

6-Chloro-9-ethylthiomethylpurine (1.5 g) and liquid ammonia (20 ml) were placed in a bomb and heated at 60° C. overnight. Evaporation of the ammonia gave a residue which was treated with cold water, filtered, and washed with cold water. This yielded 9-ethylthiomethyladenine (1.17 g) as a white solid, m.p. 140°–142° C. Recrystallization from ethanol gave white plates, m.p. 142°–143° C.

EXAMPLE 19

9-(2-Hydroxyethylthiomethyl)adenine

2-Acetoxyethanethiol was prepared according to the method of Miles and Owen, *J. Chem. Soc.*, 817 (1952). Acetic anhydride (102.1 g) was added over 1.25 hours to a mixture of 2-mercaptoethanol (78.1 g) and a 10% solution of sulfuric acid in acetic acid (3 ml). External cooling was used during the addition to keep the reaction temperature below about 40° C. After the addition of acetic anhydride was complete, the reaction mixture was heated at 65° C. for one hour and allowed to stand at room temperature overnight. Ether (500 ml) was added to the reaction mixture and the resulting solution washed with water (3×100 ml) and with brine (1×100 ml). The ether solution was dried over anhydrous sodium sulfate and sodium bicarbonate. Distillation gave 2-acetoxyethanethiol (77.5 g. bp 57°–67° C. at 10 mm hg).

Hydrogen chloride gas was introduced into a mixture of 2-acetoxyethanethiol (24.0 g) and paraformaldehyde (6.0 g) at a moderate rate with external cooling for 3 hours. Calcium chloride (25 g) was added and the reaction mixture allowed to stand in a salt-ice bath for 4 hours. Methylene chloride (200 ml) was added, the reaction mixture filtered and the solvent evaporated with rigorous exclusion of moisture. The residual oil was distilled to give 2-acetlyloxyethyl chloromethyl sulfide (18.5 g, bp 82°–87° C. at 3 mm Hg).

Following the procedure of Schaeffer, et al. *J. Med. Chem.* 14, 367 (1971), 2-acetoxyethyl chloromethyl sulfide (3.37 g) was added to a mixture of 6-chloropurine (3.09 g), triethylamine (2.23 g) and dimethylformamide (20 ml). The reaction mixture was stirred at room temperature for 90 hours and the solvent then removed under reduced pressure. The residual oil was dissolved in chloroform (30 ml) and placed on a column of Florisil (200 g) in chloroform. Elution with chloroform resulted in the desired product in 2.1 liters of eluate (after discarding the initial 300 ml collected). The solvent was evaporated to give a residual oil. Ether-pet.ether was added and the mixture chilled to give 9-(2-acetoxyethylthiomethyl)-6-chloropurine (1.4 g, mp 82°–87° C.). Recrystallization from ether gave white prisms m.p. 89°–91° C.).

9-(2-Acetoxyethylthiomethyl)-6-chloropurine (1.1 g) and ammonia (20 ml) were placed in a bomb and heated at 60° C. for 24 hours. The reaction mixture was removed from the bomb and the ammonia allowed to evaporate. The residue was triturated with cold water, filtered and washed with additional cold water. The resulting crude 9-(2-hydroxyethylthiomethyl)adenine (0.73 g) melted at 166°–169.5° C. Recrystallization from ethanol gave white plates, m.p. 170°–172° C.

EXAMPLE 20

9-(2-(3-Carboxypropionyloxy)ethoxymethyl)guanine

A mixture of 9-(2-hydroxyethoxymethyl)guanine (0.25 g), succinic anhydride (0.55 g) and pyridine (50 ml) was heated under anhydrous conditions on a steam bath overnight. The solvent was evaporated under reduced pressure at <40° C., the last trace being removed azeotropically with toluene. The residue was triturated with acetone and the product removed by filtration. Recrystallization from methanol afforded 9-(2-(3-carboxypropionyloxy)ethoxymethyl) guanine, m.p. 203°–207° C. (sinter 190° C.), in 44% yield.

EXAMPLE 21

9-Ethylthiomethyl-N-6-methyladenine

6-Chloro-9-ethylthiomethylpurine (1.2 g) and methylamine (20 ml) were placed in a bomb and heated at 60° C. for 24 hours. The excess methylamine was then allowed to evaporate at room temperature. The residue was triturated with ice water (10 ml) and filtered. Recrystallization of the tan solid from ether with charcoal (Darco 60) treatment gave 9-ethylthiomethyl-N-6-methyladenine (0.64 g), m.p. 111.5°–113° C.

EXAMPLE 22

9-(2-Aminoethoxymethyl)adenine

To a stirred, ice-bath cooled dispersion of sodium hydride (4.0 g of a 60% dispersion in mineral oil) in dimethylformamide (500 ml) was added adenine (13.5 g). After one hour, the ice-bath was removed and the mixture stirred at ambient temperature for an additional 3 hours. A solution of N-(2-chloromethoxyethyl)phthalimide (23.9 g) in dimethylformamide (100 ml) was added dropwise over 0.5 hour. The reaction mixture was stirred at ambient temperature for 18 hours and then poured with stirring over ice water (2 liters). The resulting solid was recrystallized from 2-methoxyethanol and then from dimethylformamide to give 9-(2-phthalimidoethoxymethyl)adenine (15.0 g), m.p. 256°–258° C.

A mixture of 9-(2-phthalimidoethoxymethyl)adenine (3.38 g), hydrazine hydrate (1.0 ml of an 85% aqueous solution) and ethanol (150 ml) was heated at reflux for 2 hours. 2-Methoxyethanol (50 ml) was added and refluxing continued for an additional 2 hours. The solvent was removed under reduced pressure and 1 N hydrochloric acid (50 ml) added. The mixture was stirred at ambient temperature for 30 minutes and allowed to stand at 0° C. overnight. The solution was filtered and the filtrate diluted with water (100 ml) and stirred with excess basic ion exchange resin (Rexyn 201(OH)) until a negative silver nitrate test was obtained. It was then filtered and most of the water removed under reduced pressure. The aqueous solution was cooled and the resulting solid removed by filtration. This was recrystallized from isopropanol to give 9-(2-aminoethoxymethyl)adenine (1.0 g), m.p. 170°–171° C.

EXAMPLE 23

2,6-Diamino-9-(2-acetoxyethoxymethyl)purine

Following the procedure of Example 13, 2,6-dichloro-9-(2-acetyloxyethoxymethyl)purine was converted to 2,6-diazido-9-(2-acetyloxyethoxymethyl)purine, m.p. 69°–70° C. (from ethanol water), in 83% yield. And this was catalytically reduced by hydrogen over 10% palladium on charcoal in methanol at 50 psi to give 2,6-diamino-9-(2-acetoxethoxymethyl)purine, m.p. 158°–159° C. (from ethanol), in 88% yield.

EXAMPLE 24

2-Amino-6-methylthio-9-(2-hydroxyethoxymethyl)purine

A mixture 9-(2-Hydroxyethoxymethyl)thioguanine (0.7 g), methyl iodide (0.2 ml), Dowex $HCO_3^-$ resin (1.7 g) and methanol (200 ml) was stirred overnight at room temperature. The resin was removed by filtration, washed with methanol and the combined filtration evaporated, and the residue recrystallized from isopropanol and then from acetone to give 2-amino-6-methylthio-9-(2-hydroxyethoxymethyl)purine, m.p. 188°–191° C. in 38% yield.

EXAMPLE 25

9-(3-Hydroxypropoxymethyl)guanine

Sodium benzoate (96.32 g) in DMF (690 ml) was heated to 80° C., and 1-chloro-3-hydroxypropane (63.06 g) was added over 15 minutes. The temperature increased to 135° C., and the reaction mixture was heated at 135°–175° C. for 3 hours. Filtration removed 38 g of sodium chloride (97% of theory). The filtration was partially evaporated at reduced pressure at <40° C. The concentrated filtrate was poured into ice water and extracted well with ether. The combined ether extracts were washed with water, dried over anhydrous sodium sulfate, and evaporated. The residual oil was distilled through a Vigreux column to give 3-benzoyloxy-1-propanol (85.2 g), b.p. 124°–132° C. at 0.055 mm Hg.

Anhydrous hydrogen chloride was bubbled into a solution of 3-benzoyloxy-1-propanol (15.02 g) and paraformaldehyde (2.49 g) in dichloromethane (35 ml) for 1 hour at 0° C. The solvent was evaporated under reduced pressure at <40° C. giving a 92% yield of crude 3-benzoyloxypropoxymethyl chloride which was used without purification.

A solution of trimethylsilylated guanine in benzene (25 ml) prepared as in Example 6 (from 2.0 g of guanine) containing triethylamine was heated at reflux and 3-benzoyloxypropoxymethyl chloride (2.96 g) dissolved in benzene (15 ml) was added over a 3 hour period. The reaction mixture was heated at reflux under nitrogen overnight. The solvent was removed under reduced pressure, and 95% ethanol and methanol were added to the residual oil. The mixture was heated on a steam bath for several minutes and the solvent then evaporated under reduced pressure. Chloroform (200 ml) was added and the resulting solid removed by filtration. The solid was dissolved in a minimal amount of DHF, filtered (to remove any guanine present) and reprecipitated by the addition of water. Recrystallization from methanol (with charcoaling) gave 9-(3-benzoyloxypropoxymethyl)guanine (0.94 g) as a pale yellow solid, m.p. 198°–201° C.

A mixture of 9-(3-benzoyloxypropoxymethyl)guanine (0.5 g) and aqueous 45% methylamine (10 ml) was stirred overnight at room temperature. Excess methylamine and water was evaporated at <30° C. under reduced pressure and the residue recrystallized from ethanol to give 9-(3-hydroxypropoxymethyl)guanine (0.24 g), m.p. 223° C. (with resolidification), as the .½ hydrate.

EXAMPLE 26

| Oil in Water Cream base | |
|---|---|
| 9-(2-hydroxyethoxymethyl)guanine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water | to 100.0 g |

EXAMPLE 27

| Water Soluble Ointment Base | |
|---|---|
| 2-amino-9-(2-hydroxyethoxymethyl)adenine | 0.5 g |
| Glycerol | 15.0 g |
| Macrogol 300 | 20.0 g |
| Polyethylene Glycol 1500 | 64.5 g |

EXAMPLE 28

| Tablet - (Total weight 359 mg) | |
|---|---|
| 9-(2-hydroxyethoxymethyl)guanine | 100 mg |
| Lactose | 200 mg |
| Starch | 50 mg |
| Polyvinylpyrrolidone | 5 mg |
| Magnesium Stearate | 4 mg |

EXAMPLE 29

A solution of 9(2-hydroxyethoxymethyl)guanine (4.73 g) in 97% formic acid (24 ml) was stirred at room temperature overnight. The amber solution was diluted with about 200 ml of dry ether and chilled. The resulting white precipitate was filtered, dried and recrystallized from dry dimethylformamide to give 9-(2-formyloxyethoxymethyl)guanine (3.6 g, m.p. 225°–227° C.).

EXAMPLE 30

A solution of 2-amino-9-(2-hydroxyethoxymethyl)adenine (0.5 g) in 97% formic acid (2.5 ml) was stirred in an ice bath for 3 hours, and then at room temperature overnight. Dry ether (80 ml) was added and the mixture chilled. The solid was removed by filtration and dissolved in hot acetonitrile (125 ml); residual solids were removed by filtration. The filtrate was applied to a column containing silica gel (14 g) in acetonitrile. The column was eluted with dry acetone. The eluate was evaporated and the residual solid recrystallized from acetonitrile to give 2-amino-9-(2-formyloxyethoxymethyl)adenine (93 mg, m.p. 238°–240° C.).

EXAMPLE 31

| Tablet - (Total weight 359 mg) | |
|---|---|
| 9-(2-Formyloxyethoxymethyl)guanine | 100 mg |
| Lactose | 200 mg |
| Starch | 50 mg |
| Polyvinylpyrrolidone | 5 mg |
| Magnesium stearate | 4 mg |

EXAMPLE 32

| Tablet - (Total weight 359 mg) | |
|---|---|
| 2-Amino-9-(2-formyloxyethoxymethyl)adenine | 100 mg |
| Lactose | 200 mg |
| Starch | 50 mg |
| Polyvinylpyrrolidone | 5 mg |
| Magnesium stearate | 4 mg |

The following compounds are also preferred:

| Compound | m.p. |
|---|---|
| 9-[2-(p-Fluorosulfonylbenzamido)ethoxymethyl]adenine | 201–202° C. |
| 9-(2-Bromoacetamidoethoxymethyl)adenine hydrogen oxalate | 132–133° C. |
| 9-[1-(2-Hydroxyethoxy)octyl]adenine | 121–123° C. |
| 6-Dimethylamino-9-[1-(2-hydroxyethoxy)ethyl]purine | 86–88° C. |
| 9-(2-Amino-1-methylethoxy)methyladenine dihydrochloride | 181–182° C. (eff) |
| 9-(2-Hydroxyethoxymethyl)-6-mercaptopurine | decomposes |
| 9-(2-Hydroxypropoxy)methyladenine | 164–167° C. |
| 9-(1,3-dibenzyloxy-2-propoxymethyl)adenine | 120.5–122.5° C. |

-continued

| Compound | m.p. |
|---|---|
| 9-(2-Sulfamoyloxyethoxymethyl)adenine. | 172–173.5° C. |
| 9-(2-N—Carbobenzoxyphenylalanylamidoethoxymethyl)adenine | 208–210° C. |
| 9-(1,3-Dibenzyloxy-2-propoxymethyl)-6-mercaptopurine monohydrate | 162–164° C. |
| 9-(3-Benzoylpropoxymethyl)guanine | 198–201° C. |
| 9-(2-Benzoyloxyethoxymethyl)purine | 128–130° C. |
| 9-[1-(2-Hydroxyethoxy)ethyl]guanine | >260° C. |
| 9-Ethoxymethylguanine | 275–280° C. (dec.) |
| 9-[(2-Amino-1-cyclopentylethoxy)methyl]-6-dimethylaminopurine dihydrochloride | 153–154° C. (dec.) |
| 9-[(2-Amino-1-methylethoxy)methyl]-6-dimethylaminopurine hydrochloride | 201–203° C. |
| 9-[(2-X—Carbobenzoxyphenylalanylamido-1-cyclopentylethoxy)methyl]-6-dimethylaminopurine | 146–147° C. |
| 6-Diethylamino-9-[1-(2-benzoyloxyethoxy)ethyl]purine | 83–86° C. |
| 2-Amino-6-dimethylamino-9-[1-(2-hydroxyethoxy)ethyl]purine homihydrate | 92–94° C. |
| 2-Amino-6-chloro-9-[1-(2-benzoyloxyethoxy)ethyl]purine | 125–130° C. |
| 2-Amino-6-Chloro-9-(4-benzoyloxybutoxymethyl)purine | 119–121° C. |
| 9-[(2-N—Carbobenzoxyphenylalanylazldo-1-methylmethoxy)methyl]-6-dimethylaminopurine | 149–152° C. |
| 2-Amino-9-(2-benzoyloxyethoxymethyl)purine | 149–154° C. |
| 9-(2-Benzoyloxyethoxymethyl)-2,6-diazidopurine | 124.5–125.0° C. |
| 9-Carboxymethoxymethyl-2,6-diaminopurine.0.02 2-methoxyethanol | ~250° C. (dec.) |
| 9-(4-Hydroxy-n-butoxymethyl)guanine hemihydrate | 234° C. with resolidification and decomposition |
| 6-Dimethylamino-9-(2-hydroxypropoxy)methylpurine hydrochloride | 144–146° C. |
| 9-[(2-Phenylalanylamido-1-methylethoxy)methyl]-6-dimethylaminopurine one quarter hydrate | 77–80° C. |
| 9-[(2-Phenylalanylamido-1-phenylethoxy)methyl]-6-dimethylaminopurine one quarter hydrate | sinter ~135° C. melt 142–144° C. |
| 2-Acetamido-9-(2-acetyloxyethoxymethyl)hypoxanthine | 202.5–204.5° C. |

The above compounds were prepared by the methods disclosed herein

EXAMPLE 34

Treatment of Herpes Simplex

Both eyes of a New Zealand White rabbit were infected with a suspension of the PH 8 strain of type I herpes simplex virus using the teaching of the method of Jones, B. J. Wise, J. B. and Patterson A. entitled *The measurement of enhancement or inhibition of virus replication in the cornea. Evaluation of drug effects in the eye*, 83–97. Symposium of the Royal Society of Medical, ed. Pigott, P.V., Association of Medical Advisers to the Pharmaceutical Industry, London, 1968.

One of the infected eyes of the rabbit was then treated topically beginning on the 4th day after infection with two drops of a 1% aqueous solution of 2-amino-9-(2-hydroxyethoxymethyl) adenine for a period of four days 5 times per day. On the fifth day after treatment began the treated infected eye was free of infection whereas the non-treated eye continued to exhibit the infection.

EXAMPLE 35

Treatment of Herpes Simplex

The method of Example 33 was followed except that a 1% aqueous solution of 9-(2-hydroxymethyl) guanine was administered beginning on the 3rd day after infection. The results were the same as in Example 33.

EXAMPLE 36

9-(2-Benzoyloxyethoxymethyl)-2-methylthioadenine

To a solution of 6.00 g (28.4 mmol) of 7-formamido-5-methylthiofurazano[3,4-d]pyrimidine[1] in 50 ml of dimethylformamide which was cooled on an ice bath and protected from moisture with a calcium chloride drying tube was added 3.00 g (29.7 mmol) of triethylamine. After five minutes 8.05 g (37.6 mmol) of 2-benzoyloxyethoxymethyl chloride was added along with 5 ml of dimethylformamide. An additional 1.00 g (9.9 mmol) of triethylanine was added, the ice bath was removed, and the reaction was stirred at ambient temperature overnight. The reaction was poured over 400 g of crushed ice containing 2 ml of acetic acid. The mixture was extracted with five 50 ml portions of chloroform, the combined extracts were washed with 25 ml of brine and dried (MgSO$_4$). The solvent was removed by spin evaporation in vacuo at asperator pressure and finally at about 1 mm Hg to remove the dimethylformamide. The resultant dark oil was dissolved in 200 ml of ethyl acetate and passed through a pad of superfiltrol #9. The pad was washed with two 75 ml portions of ethyl acetate. The combined filtrates and washes were spin evaporated in vacuo to give an orange oil which was a mixture (~1 to 1) of formylated and unformylated product. The oil was therefore dissolved in formic acetic anhydride (formed from 100 ml of acetic anhydride and 50 ml of 97–100% formic acid) and heated on an oil bath at 80° for two hours, left overnight at ambient temperature and then spin evaporated in vacuo to give 7-(N-formyl-2-benzoyloxyethoxymethylamino)-5-methylthiofurazano[3,4-d]pyrimidine as a crude oil. This oil was dissolved in 200 ml of acetic acid and placed on a water bath. While the solution was magnetically stirred 30 g of zinc powder was added in portions over 20 minutes. The mixture was then heated near reflux for 1.5 hr, cooled, filtered, the solids washed with acetic acid and then spin evaporated in vacuo. The residue was covered with 100 ml of water and turned on the rotoevaporator without heating until a solid formed. The aqueous layer was decanted, the solids were digested with 50 ml of ethanol and allowed to cool. The solids were collected, washed with ether and dried; yield, 3.30 g (32%), m.p. 166°–167°. Recrystallization of 0.80 g from ethanol gave the analytical sample of 9-(2-benzoyloxyethoxymethyl)-2-methylthioadenine, m.p. 166°–168°; λmax ($\epsilon \times 10^{-3}$) (10% EtOH in solvent) pH 1-270 (15.0), 300 (sh) (7.0), $H_2O$-276 (13.6), pH 13-276 (14.9) nm; nmr (DMSO-$D_6$), 2.50 (3H, S), 3.94 (2H, M), 4.40 (2H,m), 5.60 (2H, S), 7.33 (2H, S), 7.43–8.01 (5H, M), 8.16 (1H, S) δ.

1. Prepared by the general method of E. C. Taylor et al., *J. Org. Chem.*, 36, 3211 (1971).

Anal. Calc'd. for $C_{16}H_{17}N_5O_3S$: C, 53.47; H, 4.77; N, 19.49. Found: C, 53.72; H, 4.85; N, 19.56.

EXAMPLE 37

9-(2-Hydroxyethoxymethyl)-2-methylthioadenine

A mixture of 2.20 g (6.12 mmol) of 9-(2-benzoyloxyethoxymethyl)-2-methylthioadenine and 100 ml of 40% aqueous methylamine was heated on a steam bath with occasional agitation for one hour. The solution was cooled and spin evaporated in vacuo. The resultant oil was leached with five 40 ml portions of hot ether to give a solid; yield, 1.31 g (84%), m.p. 174°–176°. Recrystallization from ethanol gave the analytical sample of 9-(2-hydroxyethoxymethyl)-2-methylthioadenine; λmax ($\epsilon \times 10^{-3}$) (10% EtOH in solvent) pH 1-270 (16.7), 291 (sh) (11.9), $H_2O$ and pH 13-276 (15.2) nm; nmr (DMSO-$d_6$), 2.49 (3H, S), 3.55 (4H, S), 4.65 (1H, br S), 5.55 (2H, S), 7.31 (2H, S), 8.15 (1H, S) δ.

Anal. Calc'd. for $C_9H_{13}N_5O_2S$: C, 42.34; H, 5.13; N, 27.43. Found: C, 42.66; H, 5.10; N, 27.39.

EXAMPLE 38

9-(2-Hydroxyethoxymethyl)-2-methylthiohypoxanthina

To a stirred solution of 0.50 g (1.96 mmol) of 9-(2-hydroxyethoxymethyl)-2-methylthioadenine in 10 ml of AcOH was added 0.83 g (12.0 mmol) of $NaNO_2$ in portions over a period of 1 hour. The reaction mixture was stirred overnight, the white solids were removed by filtration and washed with a few mls of AcOH. The combined filtrates and washings were spin evaporated in vacuo to give a water soluble solid which was dissolved in 40 ml of $H_2O$. This solution was applied to an Amberlite XAD-2 column [23 cm×3 cm] which was eluted with 1000 ml of $H_2O$ to remove contaminating salts. Elution with 30% EtOH in $H_2O$ removed the product which was isolated by spin evaporation and recrystallization from EtOH; yield, 0.245 g (48%) of 9-(2-hydroxyethoxymethyl)-2-methylthiohypoxanthine, m.p. 190°–193°, λmax ($\epsilon \times 10^{-3}$) (10% EtOH in solvent) pH 1-268 (16.2), $H_2O$-262 (15.2), 284 (sh) (11.5), pH 13-272 (15.2) nm; nmr (DMSO-$d_6$), 2.58 (3H,s), 3.57 (4H,s), 4.67 (1H, br s), 5.56 (2H,s), 8.14 (1H,s), 12.52 (1H, br s) δ.

Anal. Calc'd. for $C_9H_{12}N_4O_3S$: C, 42.17; H, 4.72; N, 21.86. Found: C, 42.36; H, 4.72; N, 21.57.

EXAMPLE 39

9-(2-Hydroxyethoxymethyl)guanine

A solution of 44 mg of 9-(2-hydroxyethoxymethyl)-2-methylthiohypoxanthine in 50 ml of $NH_3$ saturated EtOH was heated in a stainless steel vessel at 140° for 60 hr. The reaction solution was spin evaporated in vacuo and the residual solid was recrystallized from EtOH; yield, 15 mg. (39%). The tlc, UV, NMR, and mass spectral data were the same as that for authentic 9-(2-hydroxyethoxymethyl)guanine prepared in Example 5.

EXAMPLE 40

9-(2-Acetyloxyethoxymethyl)guanine

A mixture of 9-(2-hydroxyethoxymethyl)guanine (4.6 g), dry dimethylformamide (46 ml), acetic anhydride (16 ml) and dry pyridine (24 ml) was stirred at room temperature overnight. The resulting white solid was removed by filtration and dissolved in warm dimethylformamide (100 ml), pyridine (10 ml) and acetic anhydride (8 ml) added and the mixture stirred for 18 hr. The white solid formed was removed by filtration, washed with ethyl acetate and recrystallized from dimethylformamide to give 9-(2-acetyloxyethoxymethyl)guanine (3.3 g), m.p. 240°–241° C.

EXAMPLE 41

9-(2-Propionyloxyethoxymethyl)guanine

A mixture of 9-(2-hydroxyethoxymethyl)guanine (1.0 g) and dry dimethylformamide (50 ml) was heated on a steam bath until most of the solid had dissolved. It was then cooled to room temperature. Dry pyridine (10 ml) and propionic anhydride (2.9 ml) was added and the mixture stirred at room temperature overnight. Additional propionic anhydride (1.0 ml) was added and the mixture stirred for an additional 18 hr. The reaction mixture was diluted with ethyl acetate, chilled and the resulting solid removed by filtration. This was recrystallized from dimethylformamide to give 9-(2-propionyloxyethoxymethyl)guanine (0.9 g), m.p. 223°–226° C.

EXAMPLE 42

9-[2-(2,2-Dimethylpropionyloxy)ethoxymethyl]guanine

A mixture of 9-(2-hydroxyethoxymethyl)guanine (2.46 g), dry pyridine (400 ml), and pivalic anhydride (6.5 ml) was heated on a steam bath for a total of 33 days. On day 11 additional pyridine (150 ml) was added, and on day 27 dimethylformamide (50 ml) was added. Volatiles were removed under reduced pressure, and the residue was triturated with ethyl acetate. The insoluble solid was removed by filtration and dissolved in methanol-acetone. Silica gel (3 g) was added and the solvent evaporated. The residue was added to a column of silica gel (180 g) in acetone. Elution with acetone yielded an initial fraction of N,O-diacylated material followed by a fraction containing the desired monoacylated product. The acetone was evaporated from this latter fraction, and the residue was recrystallized from dimethylformamide-acetonitrile-ethyl acetate to give 9-[2-(2,2-dimethylpropionyloxy)ethoxymethyl]guanine (0.5 g), m.p. 245°–246° C.

EXAMPLE 43

9-(2-Aminoethoxymethyl)guanine

A dispersion of N-(2-hydroxyethyl)phthalimide (19.1 g) and paraformaldehyde (3.0 g) in 1,2-dichloroethane (250 ml) was cooled in an ice-salt-acetone bath and saturated with dry hydrochloric acid with stirring. After 4 hours the mixture was dried over calcium chloride, filtered and evaporated under reduced pressure to give N-(2-chloromethoxyethyl)phthalimide (21.9 g), m.p. 69°–72° C.

To a stirred solution of tris trimethylsilylguanine (16.5 g) in toluene (50 ml) was added N-(2-chloromethoxyethyl)phthalimide (17.0 g) and triethylamine (23 ml). The reaction mixture was heated at reflux under nitrogen for 29 hours, cooled and evaporated under reduced pressure giving a dark brown oil. The oil was digested in ethanol (400 ml) on a steam bath for 40 minutes, giving a solid which was collected and washed with ethanol and ether. It was recrystallized from 2-methoxyethanol to give 9-(2-phthalimidoethoxymethyl)guanine hydrate (14.4 g), m.p. >240° C. (dec.). A mixture of 9-(2-phthalimidoethoxymethyl)guanine hydrate (0.94 g), hydrazine (2 ml) and ethanol (100 ml) was heated at reflux with stirring for one hour. The reaction mixture was filtered hot, and the filtrate was cooled and evaporated under reduced pressure. Ethanol was added and the mixture re-evaporated. This was repeated three times. The residual solid was stirred with 3% aqueous acetic acid (50 ml) for 30 minutes and filtered. The solids were washed with water (15 ml), and the wash and filtrate combined. The combined wash and filtrate was evaporated under reduced pressure at <35° C. to a small volume, diluted with ethanol and evaporated to dryness. The pasty, white solid was dispersed in a small amount of ethanol and diluted with a few ml ether to give a granular solid which was collected, washed with ethanol and dried. Recrystallization from ethanol-water gave 9-(2-aminoethoxymethyl)guanine acetate monohydrate (0.43 g), m.p. (~135° C. melts and resolidifies) 174°–176° C.

EXAMPLE 44

9-(2-hydroxyethoxymethyl)guanine

To a mixture of acetic anhydride (1.2 ml) and p-toluenesulfonic acid (0.09 g) was added with stirring dioxolane (1.02 g)-caution, exothermic. The solution was allowed to cool for several minutes. Diacetylguanine (1.45 g) and dry toluene (9 ml) were added and the reaction mixture was stirred at reflux for 18 hr. and then allowed to cool to room temperature. The toluene was decanted off and the residue triturated several times with benzene. Methanol (10 ml) was added to the residue and evaporated under reduced pressure. To the residue was added 40% aqueous methylamine (10 ml) and the mixture heated on a steam bath for 20 min. The water and methylamine were removed under reduced pressure, ethanol (10 ml) was added and evaporated. The residue was thoroughly extracted with boiling methanol (700 ml total) and the combined extracts evaporated. The resulting solid was triturated with cold ethanol and then recrystallized from methanol to give 9-(2-hydroxyethoxymethyl)guanine (0.3 g).

I claim:

1. A substituted purine of formula

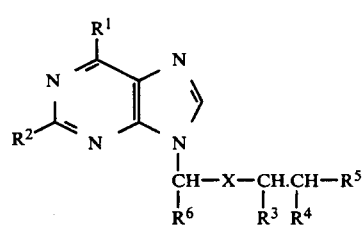

wherein X is sulphur or oxygen; $R^1$ is halogen, hydrogen, thio,alkylthio, alkoxy or azide; $R^2$ is hydrogen, halogen, amino or azide; $R^3$ is nitrogen, straight or branched chain or cyclic alkyl, hydroxyalkyl, benzyloxyalkyl or phenyl; $R^4$ is hydrogen, hydroxy, or lower alkyl; $R^5$ is hydrogen, hydroxy, amino, alkyl, hydroxyalkyl, benzoyloxy, benzoyloxymethyl, benzyloxy, sulphamoyloxy, phosphate, carboxypropionyloxy, or acetoxy; and $R^6$ is hydrogen alkyl, hydroxyalkyl or a pharmaceutically acceptable salt thereof.

2. A substituted purine of formula (I) according to claim 1 wherein X is an oxygen atom.

3. A method of treating a susceptible viral infection in a mammal which comprises administering an effective non-toxic amount of the compound or a pharmaceutically acceptable salt of claim 1.

4. The method of claim 3 in which X is oxygen.

5. The method of claim 4 in which $R^1$ is chlorine, $R^2$ is amino, $R^5$ is benzoyloxy and $R^3$, $R^4$ and $R^6$ are hydrogen.

6. The method of claim 3 in which the viral infection is a herpes virus infection.

7. The method of claim 5 in which the viral infection is a herpes virus infection.

8. A pharmaceutical composition comprising an effective anti-viral amount of the compound or salt of claim 1 and a pharmaceutically acceptable carrier therefore.

9. The composition of claim 8 in which X is oxygen.

10. The composition of claim 8 in which the amount is an effective anti-herpes amount.

11. The composition of claim 8 in a form for oral or topical administration.

12. A compound of formula (I)

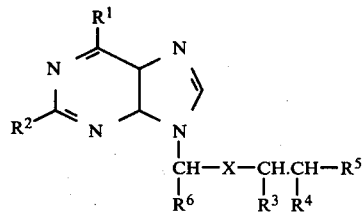

wherein $R^1$ is chlorine, $R^2$ is amino, $R^5$ is benzoyloxy and $R^3$, $R^4$ and $R^6$ are each hydrogen or a pharmaceutically acceptable salt thereof, wherein X is oxygen.

13. A method of treating a susceptible viral infection in a mammal which comprises administering an effective non-toxic amount of the compound or salt of claim 12.

14. A pharmaceutical composition comprising an effective anti-viral amount of the compound or salt of claim 12 and a pharmaceutically acceptable carrier therefor.

15. The compound of the formula I

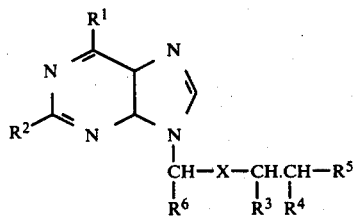

(I)

wherein X is sulphur or oxygen; $R^1$ is hydrogen, halogen, hydroxy, alkoxy, azide, thio, or alkylthio; $R^2$ is hydrogen, halogen, alkylthio, amino or azide, provided $R^2$ is not amino when $R^1$ is hydroxy; $R^3$ is hydrogen, straight or branched chain or cyclic alkyl, hydroxyalkyl, benzyloxyalkyl or phenyl, $R^4$ is hydrogen, hydroxy or alkyl; $R^5$ is hydrogen hydroxy, amino, alkyl, hydroxyalkyl, benzyloxy, benzoyloxy, benzoyloxymethyl, sulphamoyloxy, phosphate, or straight or branched chain or cyclic acyloxy having from 1 to 8 carbon atoms; $R^6$ is hydrogen or alkyl; or a pharmaceutically acceptable salt thereof.

16. The compound or salt of claim 15 wherein $R^5$ is straight or branched chain or cyclic acyloxy having from 1 to 8 carbon atoms.

* * * * *

UNITED STATES PATENT AND TRADEMARK OFFICE
CERTIFICATE OF CORRECTION

PATENT NO. : 4,360,522
DATED : November 23, 1982
INVENTOR(S) : Howard J. Schaeffer It is certified that error appears in the above-identified patent and that said Letters Patent are hereby corrected as shown below:

In the claims:

Claim 1, Column 24, line 15: Delete "nitrogen" and substitute

--hydrogen-- line 21: After "hydrogen" insert --,--

Claim 8, Column 24, line 42: Delete "fore" and substitute --for--

Claim 15, Column 26, line 5: After "hydrogen" insert --,--.

Signed and Sealed this

Sixteenth Day of April 1985

[SEAL]

Attest:

DONALD J. QUIGG

Attesting Officer      Acting Commissioner of Patents and Trademarks